(12) United States Patent
Dresser et al.

(10) Patent No.: US 10,779,908 B2
(45) Date of Patent: Sep. 22, 2020

(54) SYSTEMS AND METHOD FOR PROTECTION OF OPTICAL SYSTEM OF LASER-BASED APPARATUS

(71) Applicant: Convergent Dental, Inc., Natick, MA (US)

(72) Inventors: Charles H. Dresser, Bethel, ME (US); Nathan P. Monty, Shrewsbury, MA (US)

(73) Assignee: Convergent Dental, Inc., Needham, MA (US)

( * ) Notice: Subject to any disclaimer, the term of this patent is extended or adjusted under 35 U.S.C. 154(b) by 0 days.

(21) Appl. No.: 14/755,814

(22) Filed: Jun. 30, 2015

(65) Prior Publication Data
US 2015/0342704 A1 Dec. 3, 2015

Related U.S. Application Data

(63) Continuation of application No. 14/554,451, filed on Nov. 26, 2014.

(60) Provisional application No. 61/909,896, filed on Nov. 27, 2013.

(51) Int. Cl.
| | | |
|---|---|---|
| *A61C 1/00* | (2006.01) | |
| *A61C 19/00* | (2006.01) | |
| *A61B 18/20* | (2006.01) | |
| *A61B 18/00* | (2006.01) | |

(52) U.S. Cl.
CPC .......... *A61C 1/0084* (2013.01); *A61C 1/0046* (2013.01); *A61C 1/0061* (2013.01); *A61C 19/002* (2013.01); *A61B 2018/0097* (2013.01); *A61B 2018/20359* (2017.05)

(58) Field of Classification Search
CPC ...... A61B 18/20–18/28; A61N 5/06–2005/073
See application file for complete search history.

(56) References Cited

U.S. PATENT DOCUMENTS

| | | | |
|---|---|---|---|
| 4,674,497 A | 6/1987 | Ogasawara | |
| 4,826,431 A | 5/1989 | Fujimura et al. | |
| 5,051,823 A | 9/1991 | Cooper et al. | |
| 5,370,649 A * | 12/1994 | Gardetto | A61B 18/24 |
| | | | 606/15 |

(Continued)

FOREIGN PATENT DOCUMENTS

| | | |
|---|---|---|
| CA | 2873426 A1 | 11/2013 |
| EP | 2520221 A1 | 11/2012 |

(Continued)

OTHER PUBLICATIONS

International Search Report and Written Opinion for International Patent Application No. PCT/US2014/067601 dated Feb. 11, 2015 (9 pages).

(Continued)

*Primary Examiner* — Jonathan T Kuo
(74) *Attorney, Agent, or Firm* — Goodwin Procter LLP

(57) ABSTRACT

In an apparatus for directing a laser beam to a dental treatment area, where the apparatus includes a hand piece having an optical subsystem including a turning mirror for directing a laser beam to a treatment area via an orifice of the hand piece, a fluid supply subsystem creates a fluid flow within the hand piece proximate the turning mirror so as to mitigate contamination thereof.

12 Claims, 5 Drawing Sheets

(56) References Cited

U.S. PATENT DOCUMENTS

| | | | |
|---|---|---|---|
| 5,388,987 A | | 2/1995 | Badoz et al. |
| 5,388,988 A | | 2/1995 | Goisser et al. |
| 5,409,376 A | | 4/1995 | Murphy |
| 5,449,290 A | | 9/1995 | Reitz |
| 5,458,594 A | * | 10/1995 | Mueller ............... A61C 1/0046 606/15 |
| 5,474,449 A | * | 12/1995 | Loge .................... A61C 1/0046 433/126 |
| 5,836,941 A | * | 11/1998 | Yoshihara .............. A61B 18/24 600/108 |
| 6,231,567 B1 | | 5/2001 | Rizoiu et al. |
| 6,709,269 B1 | | 3/2004 | Altshuler |
| 7,267,672 B2 | | 9/2007 | Altshuler et al. |
| 9,089,928 B2 | * | 7/2015 | Zediker .................... E21B 29/02 |
| 2006/0116669 A1 | | 6/2006 | Dolleris |
| 2007/0016176 A1 | | 1/2007 | Boutoussov et al. |
| 2007/0224571 A1 | * | 9/2007 | Watson .................. A61B 1/253 433/31 |
| 2010/0261132 A1 | | 10/2010 | Widen |
| 2011/0189628 A1 | * | 8/2011 | Monty ................. A61C 1/0046 433/29 |
| 2013/0059264 A1 | * | 3/2013 | Monty ................. A61C 1/0046 433/29 |
| 2013/0144281 A1 | * | 6/2013 | Lewinsky .............. A61B 18/20 606/16 |
| 2014/0231085 A1 | * | 8/2014 | Zediker .................... E21B 29/02 166/288 |
| 2014/0363784 A1 | * | 12/2014 | Monty ................. A61C 1/0046 433/29 |

FOREIGN PATENT DOCUMENTS

| | | |
|---|---|---|
| JP | 2001346891 A | 12/2001 |
| JP | 2013500790 A | 1/2013 |
| WO | WO-1995025476 A1 | 9/1995 |
| WO | WO-2011014802 A2 | 2/2011 |
| WO | WO-2013/033710 A2 | 3/2013 |
| WO | WO-2014/123904 A2 | 8/2014 |

OTHER PUBLICATIONS

Synchro REPLA:Y Multi-Wavelength Workstation, (2016), 4 pages, downloaded from http://dekamedinc.com/products/synchro-replay/synchro-replay-overview/.

Yoshida, Opelaser Pro, (2016), 1 page, downloaded from http://yoshida-net.com.jp/en/products/lasers/opelaser_pro/new_p04.html.

Office Action for related Japanese Patent Application No. 2016-534195, dated Aug. 16, 2018 (4 pages), including English translation (6 pp.).

Ertl, et al., "Hard Tissue Ablation With Pulsed CO2 Lasers", SPIE vol. 1800 pp. 176-181 (.

Gerold K.H. Eyrich, "Laser-osteotomy induced changes in bone", Medical Laser Application 20 (2005) 25-36.

M. Frentzen, et al., "Osteotomy with 80μs CO2 laser pulses—histological results", Lasers Med Sci (2003)18:119-124.

Werner, et al., "CO2 laser free-form processing of hard tissue", Therapeutic Laser Applications and Laser-Tissue Interactions III, Feb. 24, 2010 vol. 6632 663202-1-663202-6.

Ivanenko, et al., Ablation of hard bone tissue with puled CO2 Lasers, Medical Laser Application 20 (2005) 13-23.

G. D. Rajitha Gunaratne, Riaz Khan, Daniel Fick, Brett Robertson, Narendra Dahotre & Charlie Ironside (2016): A review of the physiological and histological effects of laser osteotomy, Journal of Medical Engineering & Technology, DOI: 10.1080/03091902.2016. 1199743 (published online Jun. 27, 2016).

Ivanenko, et al., "Hard tissue ablation with sub-μs CO2 laser pulses with the use of air-water spray", Optical Biopsy and Tissue Optics, Proceedings of SPIE vol. 4161 (2000).

Ivanenko, et al., "In Vivo animal trials with a scanning CO2 laser Osteotome," Lasers in Surgery and Medicine 37:144-148 (2005).

Ivanenko, et al., "System development and clinical studies with a scanning CO2 laser osteotome," Optical Interactions with Tissue and Cells XVII, Proc. of SPIE vol. 6084, 60840H, (2006) 1605-7422.

Kahrs, et al., "Planning and simulation of microsugrical laser bone ablation," Int J CARS (2010) 5:155-162 (DOI 10.1007/s11548-009-0303-4).

Kuttenberger, et al., "Bone healing of the sheep tibia shaft after carbon dioxide laser osteotomy; histological results," Lasers Med Sci (2010) 25:239-249 (DOI 10.1007/s10103-009-0714-z).

Nair, et al., "Observations on pulpal response to carbon dioxide laser drilling of dentine in healthy human third molars," Lasers in Medical Science (2005) 19: 240-247 (DOI 10.1007/s10103-004-0317-7).

Werner, et al., "CO2 laser "milling" of hard tissue" Optical Interactions with Tissue and Cells XVIII, Proc. of SPIE vol. 6435, 64350E, (2007) 1605-7422.

Zhang, et al., "Optimization of Line Cut Strategy for Bone tissue ablation using Short-pulsed CO2 laser based on thermal relaxation,".

Kuttenberger, et al., "Computer-Guided CO2-laser osteotomy of the SheepTibia: Technical prerequisites and first resultes," Photomedicine and Laser Surgery, vol. 26, No. 2, 2008, pp. 129-136 (DOI: 10.1089/pho.2007.2139).

* cited by examiner

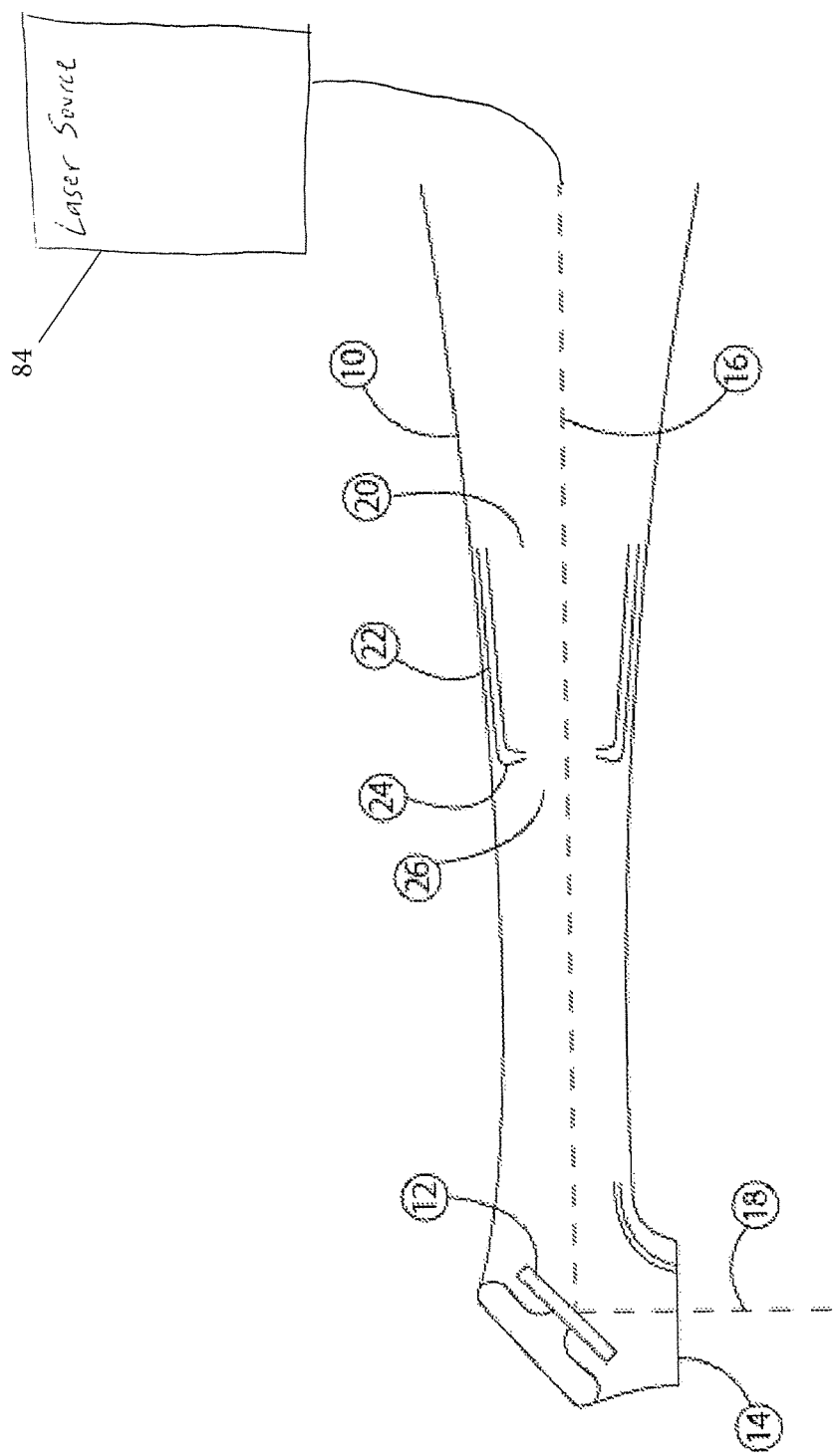

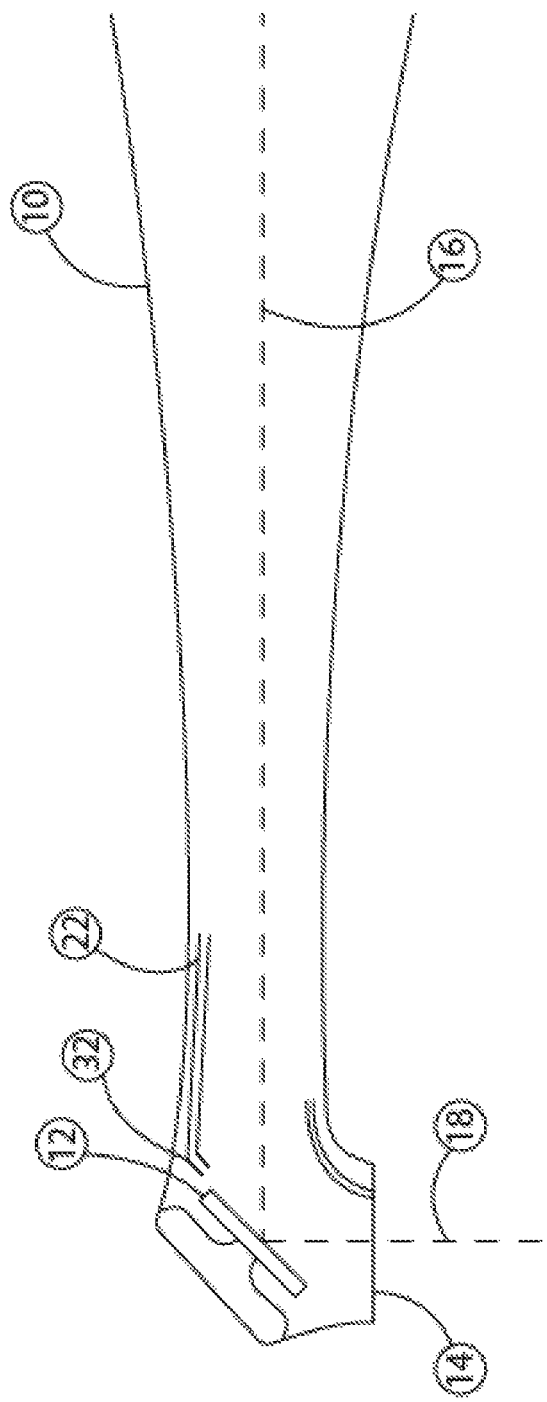

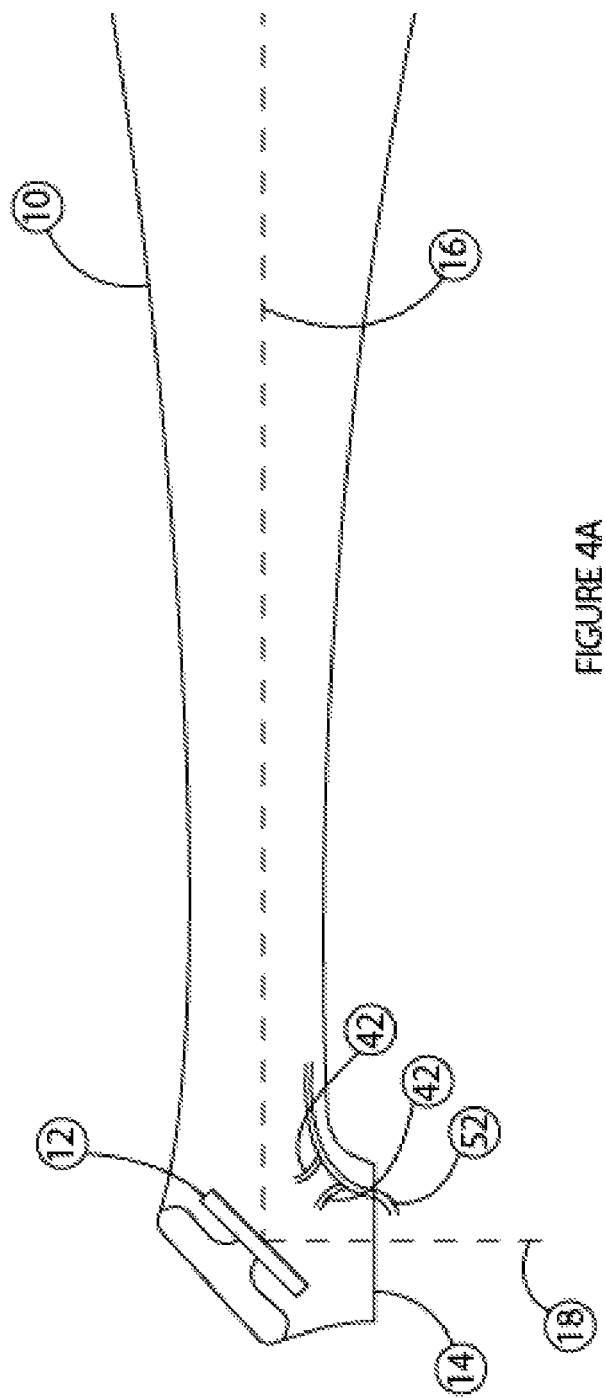

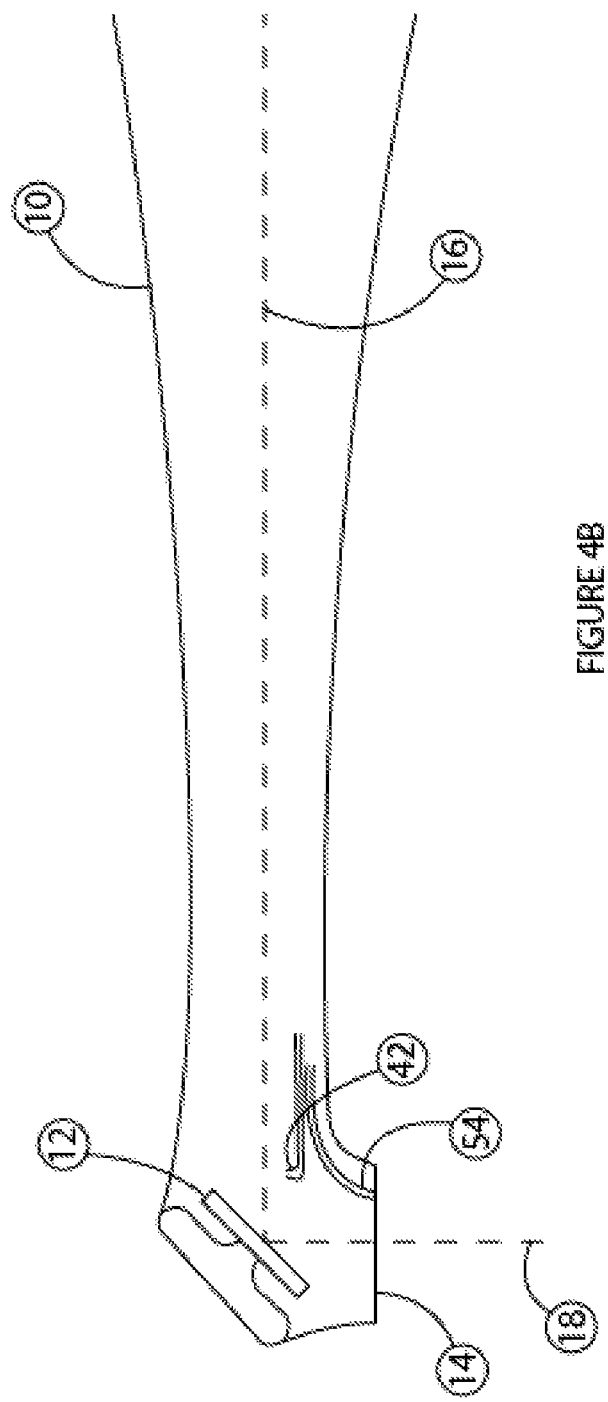

SYSTEMS AND METHOD FOR PROTECTION OF OPTICAL SYSTEM OF LASER-BASED APPARATUS

CROSS-REFERENCE TO RELATED APPLICATIONS

This application is a continuation of and claims benefit of priority to U.S. patent application Ser. No. 14/554,451 entitled "Systems and Method for Protection of Optical System of Laser Based Apparatus," filed on Nov. 26, 2014, and claims benefit of priority to U.S. Provisional Patent Application No. 61/909,896, entitled "Dental Laser with Optical System Protection," filed on Nov. 27, 2013, the contents of each of which are incorporated herein by reference in their entireties.

FIELD OF THE INVENTION

The present disclosure generally relates to a dental laser hand piece for use with a dental laser ablation system and, in particular, to systems for cleansing optical components located in the hand piece.

BACKGROUND OF THE INVENTION

FIG. 1 shows a cross-sectional view of a hand piece 10, used for dental laser treatment, such as that described in U.S. Patent Application Publication No. 2013/0059264 entitled Laser Based Computer Controlled Dental Preparation System, the contents of which are incorporated herein by reference in their entirety. The hand piece 10 includes an optical subsystem that includes a reflector 12, and the hand piece 10 has an orifice 14 through which a laser beam can exit. In particular, the reflector 12 can reflect the laser beam incident from a first optical axis 16 to a second optical axis 18, and can direct the laser beam through the orifice 14. The optical subsystem may include additional similar or different optical elements that are located inside the hand piece 10. For example, the optical subsystem may include one or more lenses for focusing the laser beam, one or more mirrors, one or more beam splitters, etc.

Treatment of dental hard tissue using a laser beam, which typically causes ablation of the tissue, can result in the formation of debris. A plasma plume may also form during ablative laser treatment of hard tissue. Often, such debris may be ejected adjacent to the plasma plume at high speeds and high temperatures.

During treatment, the orifice 14 of the hand piece is generally disposed parallel and open to a treatment area, placing the reflector 12 in close proximity to the treatment area. For example, the reflector 12 can be within 0.5-2 inches (or about 1-5 cm), or up to 3 inches (or about 7 cm) from the surface of the tissue to be treated. As such, contaminants such as debris, water, and other substances that may form in or around the mouth during treatment may enter the hand piece 10 through the orifice 14 or through other openings. Such debris can settle on one or more components of the optical subsystem and may reduce the efficiency thereof, and may even render the optical subsystem non-functional. Frequently removing the optical subsystem from the hand piece 12 and replacing the optical subsystem after cleaning it, or installing a new subsystem, can be cumbersome and costly, if not impossible.

SUMMARY OF THE INVENTION

Various embodiments described herein feature systems and methods that avoid, or at least reduce, contamination of an optical subsystem mounted or disposed inside a hand piece from debris generated during laser-based treatment provided using the hand piece. This is achieved, at least in part, using a fluid supply subsystem to create a fluid flow within the hand piece and proximate a turning mirror included in an optical subsystem disposed in the hand piece. During treatment, if any debris reaches inside the hand piece the flow of the fluid (e.g., air) can prevent such debris, or at least reduce the amount thereof, from attaching to any components of the optical subsystem including the turning mirror. Alternatively, or in addition, the fluid flow can cause any debris attached to the components of the optical subsystem to be blown away. This can avoid or reduce contamination of the optical subsystem, and greatly reduce the frequency at which the optical subsystem including the turning mirror needs to be removed from the hand piece for cleansing.

Accordingly, in to one aspect, an apparatus for directing a laser beam to a dental treatment area includes a hand piece having an optical subsystem for directing a laser beam to a treatment area via an orifice of the hand piece. The optical subsystem includes a turning mirror. The apparatus also includes a fluid supply subsystem for creating a fluid flow within the hand piece, proximate the turning mirror so as to mitigate contamination of the turning mirror. Mitigation of contamination can be indicated by maintenance of reflectivity resulting in an increase in the lasing time, which is typically the total time for which the mirror receives and reflects laser radiation with sufficient reflectivity, e.g., at least 40%, or 50%, or 60%, or 75% reflectivity, so that transmission of the laser beam to a treatment area is not significantly adversely affected and cleansing and/or replacement of the mirror is not necessary.

The hand piece may include at least a portion of the fluid supply subsystem, e.g. one or more conduits and/or one or more nozzles. In some embodiments, the fluid supply subsystem includes a conduit and a nozzle for directing a pressurized flow of a fluid directly toward the turning mirror. Alternatively or in addition, the fluid supply subsystem may include a conduit and a nozzle for directing a pressurized flow of a fluid transversely across the conduit. In some embodiments the fluid is or includes air, while in other embodiments the fluid includes one or more gas and/or a liquid. A cleansing agent such as soap may be added to the fluid.

In certain embodiments, the fluid supply subsystem or at least a portion thereof (e.g., a compressor, one or more conduits, and/or one or more nozzles) is located upstream of the turning mirror. The fluid supply subsystem may be adapted to pressurize an internal cavity of the hand piece. The fluid supply subsystem may be adapted to direct an air curtain across the orifice of the hand piece. The optical subsystem may be configured such that no optical element (e.g., a mirror, a lens, etc.) is positioned downstream of the turning mirror. In some embodiments, the apparatus also includes a radio frequency (RF) excited CO2 laser filled with gas at a pressure in a range of about 260 to 600 Torr, for generating the laser beam.

In another aspect, a method of protecting during treatment an optical subsystem of a laser-based treatment system includes directing a laser beam to a treatment area via a hand piece. The hand piece includes a turning mirror that is positioned to direct the laser beam to the treatment area through an orifice of the hand piece. The hand piece may optionally include other optical elements such as mirrors, lenses, beam splitters, etc. The method also includes generating, using a fluid supply subsystem, a fluid flow within the hand piece and proximate the turning mirror, so as to mitigate contamination of the turning mirror.

The hand piece may include at least a portion of the fluid supply subsystem, e.g., one or more conduits and/or one or more nozzles. In some embodiments, the fluid supply subsystem includes a conduit and a nozzle, and generating the fluid flow may include directing a pressurized flow of a fluid through the nozzle directly toward the turning mirror. Alternatively or in addition generating the fluid flow may include directing a pressurized flow of a fluid through the nozzle transversely across the turning mirror. The fluid may include only air or may include one or more gases, one or more liquids and/or one or more additives such as soap.

In some embodiments, the fluid supply subsystem is disposed upstream of the turning mirror. Generating the fluid flow may include pressurizing an internal cavity of the hand piece. The method may additionally include directing an air curtain across the orifice of the hand piece using the fluid supply subsystem. In some embodiments, the optical subsystem is configured such that no optical element is disposed downstream of the turning mirror. In some embodiments, the method includes generating the laser beam using a radio frequency (RF) excited $CO_2$ laser filled with gas at a pressure in a range of about 260 to 600 Torr.

BRIEF DESCRIPTION OF THE FIGURES

Various features and advantages of the present invention, as well as the invention itself, can be more fully understood from the following description of the various embodiments, when read together with the accompanying drawings, in which:

FIGS. 2 and 3 depict a cross-section of a hand piece that includes a turning mirror, and a nozzle for directing a fluid flow so as to prevent or at least reduce fouling of the turning mirror, according to different embodiments;

FIG. 4A depicts a cross-section of a hand piece that includes a turning mirror, a nozzle for directing a fluid flow so as to prevent or at least reduce fouling of the turning mirror, and a nozzle for an air curtain, according to one embodiment; and FIG. 4B depicts a cross-section of a hand piece that includes a turning mirror, a nozzle for directing a fluid flow so as to prevent or at least reduce fouling of the turning mirror, and a nozzle for a coolant, according to one embodiment.

DETAILED DESCRIPTION

Figure 1:
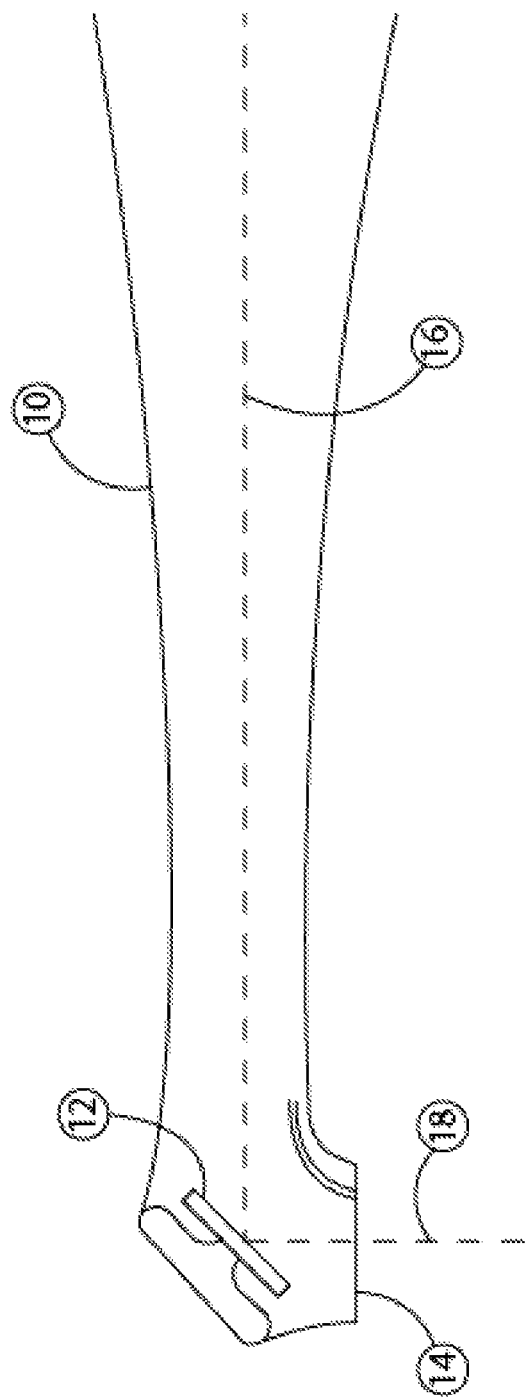
FIG. 1 depicts a cross-section of a hand piece that includes a turning mirror.

With reference to FIG. 2, a fluid supply subsystem 20 includes one or more conduits, such as tubes 22, and one or more nozzles 24. For example, the fluid supply subsystem 20 can provide a positive pressure within the hand piece 10, creating a high pressure cavity 26 therein. Due to a high pressure in the cavity 26, fluid (e.g., air) may flow substantially continuously within the hand piece 10 and out of the orifice 14. The fluid flow can impart forces opposing any contaminants ejected into the hand piece 10 through the orifice 14, or otherwise directed toward the reflector (e.g., a turning mirror) 12. The fluid flow out of the orifice is generally a function of fluid pressure and size of the orifice. For an exemplary orifice that is about 2.5 mm in diameter, a fluid pressure in the cavity 26 in a range from about 10 psi up to about 100 psi can significantly minimize the amount of debris attaching and/or remaining attached to the reflector 12. For example, without the fluid pressure a turning mirror of a diameter of about 5 mm can become sufficiently contaminated so as to prevent effective treatment in about one minute of usage. In some embodiments, the diameter of the mirror can be smaller, e.g., about 2 mm and in other embodiments the diameter can be larger, e.g., about 7 mm, 10 mm, etc. Mirrors of non-circular shapes of comparable area may be used in some embodiments. With the pressure in the cavity, the rate of contamination can be reduced such that the turning mirror can reflect and redirect the laser beam, without having to be removed from the hand piece 10 and cleansed, from at least two minutes up to about 20 minutes of lasing time, e.g., the total time for which the mirror receives and reflects laser radiation with sufficient reflectivity, e.g., at least 40%, or 50%, or 60%, or 75% reflectivity, so that transmission of the laser beam to a treatment area is not significantly adversely affected and cleansing and/or replacement of the mirror is not necessary. Pressure is generated in a range from about 10 psi up to about 100 psi. Such a flow can be created using fluid compressed using a commercially available air compressor (e.g., Gardner Denver Thomas 415ZC36/24) and regulator (e.g., SMC NARM1000-2A1-NOIG).

With reference to FIG. 3, a pressurized fluid flow within the hand piece 10 is directed transversely over or across the reflector (e.g., turning mirror) 12 using the nozzle 32. The pressurized fluid flow can impart forces upon contaminants that are on or near the surface of the reflector 12, preventing at least some contaminants from adhering to a surface of the reflector 12 and/or removing at least some contaminants attached thereto. After the laser beam is reflected by the reflector or turning mirror 12, no other optical component such as another mirror, a lens, a beam splitter, etc., interferes with or affects the laser beam, and the laser beam may directly impinge upon the targeted treatment area.

An exemplary pressure supplied to the nozzle 32 is about 55 psi for a typical nozzle size of about 1 mm in diameter. Air or pure nitrogen may be supplied to the nozzle 32 to create the transverse fluid flow. In some embodiments, the fluid may include steam; a combination of two more gases; and a combination of a gas and a liquid, such as water, soap water, a diluted weak acid/base, a diluted solvent, etc. The transverse fluid flow can also decrease the rate of contamination of the turning mirror or reflector 12, as described above.

With reference to FIGS. 4A and 4B, a pressurized fluid flow is generated within the hand piece 10 and is directed toward a surface of the reflector (e.g., turning mirror) 12 using one or more nozzles 42. The fluid may include a gas, such as air, nitrogen, or steam; a combination of two more gases; and a combination of a gas and a liquid, such as water, soap water, a diluted weak acid/base, a diluted solvent, etc. The pressurized flow of both the liquid and the gas may provide for removal of contaminants from the optical subsystem, as well as cleaning or rinsing of the optical subsystem components. A nozzle 52 receiving an air supply from the fluid supply subsystem can form an air curtain transversely across the orifice 14, minimizing the likelihood of any debris entering into the hand piece 10. Alternatively, or in addition, a nozzle 54 receiving one or more fluids from the fluid supply subsystem can deliver a coolant, such as a mist, to the treatment area.

During a typical dental treatment procedure, a pulsed laser beam may be generated and directed to a dental treatment area via the hand piece 10. If the fluid flow according to various embodiments described above includes one or more gases only, the fluid flow can be maintained continuously ON during the course of the treatment because the gas flow is not likely to interfere with the laser beam. If the fluid flow includes a liquid and/or an additive such as soap, the fluid flow can interfere with the laser beam by absorbing at least some of the laser energy. Therefore, to minimize such interference, the fluid flow or at least the flow of liquid and/or additives may be switched OFF during a burst of pulses and may be turned ON when substantially no laser pulses are delivered during a period between two consecutive laser pulse bursts.

Laser radiation at wavelengths in a range from about 9.3 µm up to about 9.6 µm can be effective in various dental and/or surgical procedures including cutting of hard dental tissue and/or a bone. To generate efficiently laser radiation at these wavelengths, in the form of pulses having widths in a range from about 1 µs up to about 30 µs, or up to about 100 µs, or up to about 250 µs, or even up to about 500 µs, a radio frequency (RF) excited $CO_2$ laser operated using gas at a pressure in a range of about 260 Torr to about 600 Torr may be used. Such a laser is described in U.S. Patent Application Pub. No. 2011-0189628A1, the contents of which are incorporated herein by reference in their entirety. Various pulse delivery patterns of the laser beam, which include a sequence of bursts of laser pulses, are described in co-pending U.S. patent application Ser. No. 14/172,562, entitled "Dental Laser Apparatus and Method of Use with Interchangeable Hand Piece and Variable Foot Pedal," filed on Feb. 4, 2014, the entire contents of which are incorporated herein by reference in their entirety, including the description of laser source 84.

The peak reflectivity of the mirrors used in various embodiments in the mid to far infrared (e.g., 8-12 µm) range can be at least 90%. During operation, the reflectivity may decrease down to about 50%, e.g., due to contamination, when the reduced reflectivity can interfere with the delivery of the laser beam and cleansing or replacement of the mirror may be needed. Directing a fluid flow in proximity of the mirror according to various embodiments described herein can maintain a reflectivity of at least 75% during a typical dental treatment session. As such, the lasing time of the mirror can be increased from about 1 minute without employing such a fluid flow up to about 2 minutes, 5 minutes, 10, minutes, and even up to about 20 minutes, within a tolerance of e.g. 1 s, 5 s, 10 s, 30 s, etc., by employing the fluid flows described in various embodiments.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions can be made by those skilled in the art without departing from the spirit and scope of the invention. Accordingly, the appended claims shall not be limited by the particular features that have been shown and described, but shall be construed also to cover any obvious modifications and equivalents thereof.

What is claimed is:

1. An apparatus for directing a laser beam to a dental treatment area, the apparatus comprising:
    a laser source adapted to generate a laser beam;
    a hand piece comprising an optical subsystem including a turning mirror comprising a planar reflective surface for directing the laser beam out of an exit orifice of the hand piece to a treatment area, wherein the exit orifice of the hand piece is located downstream of the turning mirror; and
    a fluid supply subsystem comprising:
    a fluid consisting essentially of a gas;
    a plurality of first nozzles, each first nozzle forming a corresponding outlet aperture, for creating a pressurized fluid from the fluid consisting essentially of a gas within the hand piece upstream of the turning mirror and for causing substantially continuous fluid flow past the turning mirror and out of the exit orifice of the hand piece so as to mitigate contamination of the turning mirror; and
    a second nozzle forming an outlet aperture for directing a second nozzle fluid to the treatment area,
    wherein the outlet apertures of the first nozzles terminate upstream of the turning mirror and the outlet aperture of the second nozzle terminates at least at the exit orifice.

2. The apparatus of claim 1, wherein the hand piece comprises at least a portion of the fluid supply subsystem.

3. The apparatus of claim 1, wherein the second nozzle fluid comprises a gas and a liquid.

4. The apparatus of claim 1, wherein the laser source comprises a radio frequency (RF) excited $CO_2$ laser filled with gas at a pressure in a range of about 260 to 600 Torr, for generating the laser beam.

5. The apparatus of claim 1, wherein the plurality of first nozzles positively pressurize a cavity of the hand piece to cause the substantially continuous fluid flow past the turning mirror.

6. The apparatus of claim 5, wherein the plurality of first nozzles are disposed remotely from and upstream of the turning mirror.

7. A method of protecting during treatment an optical subsystem of a treatment system, the method comprising:
    directing a laser beam to a treatment area via a hand piece comprising a turning mirror comprising a planar reflective surface that is positioned to direct the laser beam out of an exit orifice of the hand piece to the treatment area, wherein the exit orifice of the hand piece is located downstream of the turning mirror;
    generating upstream of the turning mirror, using a plurality of first nozzles of a fluid supply subsystem, each first nozzle forming an outlet aperture that terminates upstream of the turning mirror, a pressurized fluid consisting essentially of a gas within the hand piece causing substantially continuous fluid flow past the turning mirror and out of the exit orifice of the hand piece so as to mitigate contamination of the turning mirror: and
    directing, using a second nozzle of the fluid supply system forming an outlet aperture that terminates at least at the exit orifice, a second nozzle fluid to the treatment area.

8. The method of claim 7, wherein the hand piece comprises at least a portion of the fluid supply subsystem.

9. The method of claim 7, wherein the second nozzle fluid comprises a gas and a liquid.

10. The method of claim 7, further comprising generating the laser beam using a laser source comprising a radio frequency (RF) excited $CO_2$ laser filled with gas at a pressure in a range of about 260 to 600 Torr.

11. The method of claim 7, wherein the plurality of first nozzles positively pressurize a cavity of the hand piece to cause the substantially continuous fluid flow past the turning mirror.

12. The method of claim 11, wherein the plurality of first nozzles are disposed remotely from and upstream of the turning mirror.

\* \* \* \* \*